United States Patent
Cash

(10) Patent No.: US 10,980,462 B2
(45) Date of Patent: Apr. 20, 2021

(54) MICRO-VOLUME BLOOD TRANSFER DEVICE

(71) Applicant: William Phillip Cash, Marietta, GA (US)

(72) Inventor: William Phillip Cash, Marietta, GA (US)

(73) Assignee: HUMMINGBIRD MED DEVICES, INC., Marietta, GA (US)

( * ) Notice: Subject to any disclaimer, the term of this patent is extended or adjusted under 35 U.S.C. 154(b) by 0 days.

(21) Appl. No.: 14/354,363

(22) PCT Filed: Oct. 26, 2012

(86) PCT No.: PCT/US2012/062310
§ 371 (c)(1),
(2) Date: Apr. 25, 2014

(87) PCT Pub. No.: WO2013/063529
PCT Pub. Date: May 2, 2013

(65) Prior Publication Data
US 2014/0296745 A1      Oct. 2, 2014

Related U.S. Application Data

(60) Provisional application No. 61/551,577, filed on Oct. 26, 2011.

(51) Int. Cl.
*A61B 5/15* (2006.01)
*A61B 5/153* (2006.01)
*A61B 5/021* (2006.01)
*A61B 5/0215* (2006.01)

(52) U.S. Cl.
CPC .... *A61B 5/150946* (2013.01); *A61B 5/15003* (2013.01); *A61B 5/153* (2013.01); *A61B 5/150038* (2013.01); *A61B 5/150992* (2013.01); *A61B 5/0215* (2013.01); *A61B 5/02141* (2013.01); *A61B 5/150213* (2013.01)

(58) Field of Classification Search
CPC . A61B 5/1405; A61B 5/150992; A61B 5/153; A61B 5/150946; A61B 5/150038
See application file for complete search history.

(56) References Cited

U.S. PATENT DOCUMENTS

| | | | | |
|---|---|---|---|---|
| 5,053,003 A | * | 10/1991 | Dadson | A61M 1/28 604/28 |
| 5,795,340 A | * | 8/1998 | Lang | A61M 5/14 604/248 |
| 2005/0054949 A1 | * | 3/2005 | McKinnon | A61B 5/1405 600/576 |
| 2009/0157051 A1 | * | 6/2009 | Appling | A61M 25/003 604/528 |

\* cited by examiner

*Primary Examiner* — Daniel L Cerioni
*Assistant Examiner* — Yasmeen S Warsi
(74) *Attorney, Agent, or Firm* — Eric B. Alspaugh, APC

(57) ABSTRACT

A micro-volume blood transfer device to facilitate the collection of small volumes of clean arterial blood from patients who may be volume restricted for blood loss such as low-birth weight infants.

9 Claims, 1 Drawing Sheet

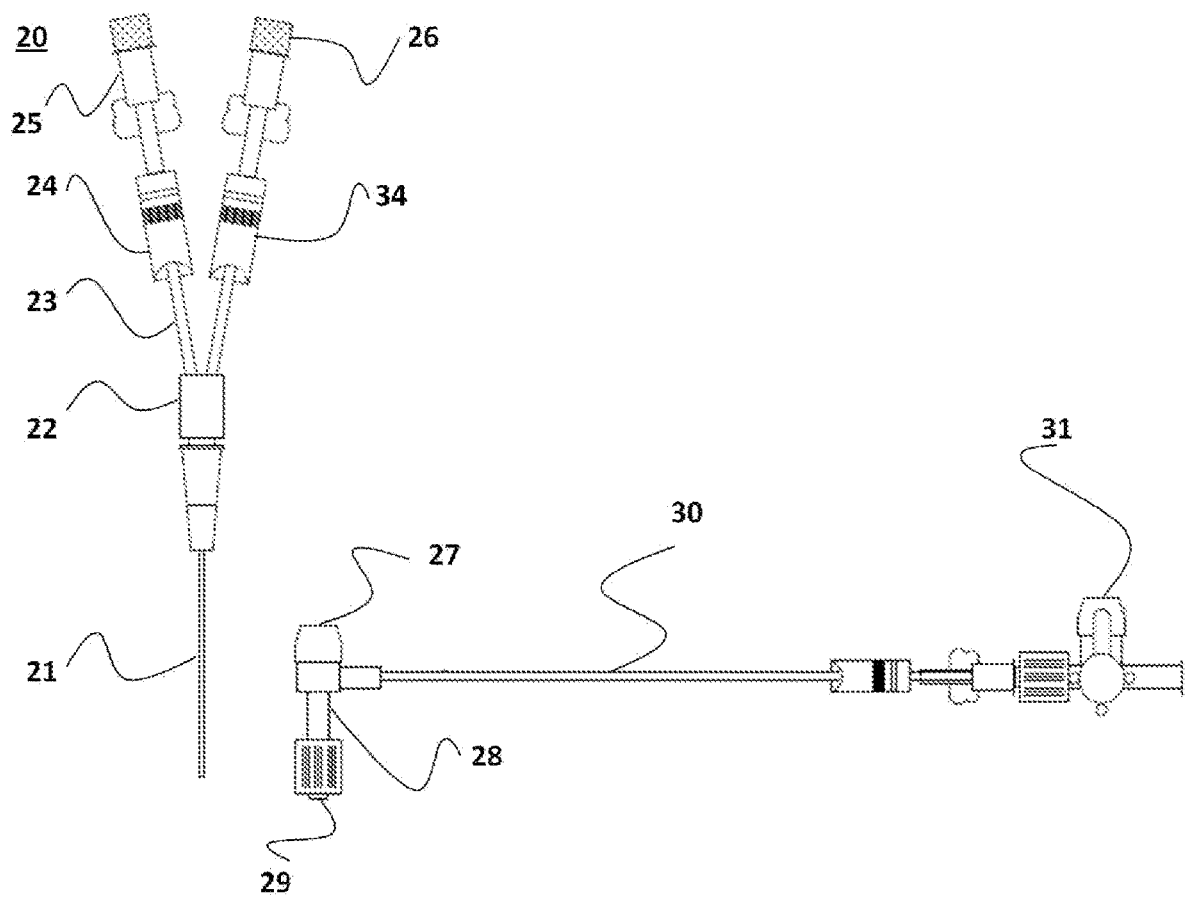

MICRO-VOLUME BLOOD TRANSFER DEVICE

CROSS-REFERENCE TO RELATED APPLICATION

This application claims priority to PCT Application number PCT/US12/62310 filed on Oct. 26, 2012 and U.S. provisional application No. 61/551,577 filed Oct. 26, 2011 the contents of which are hereby incorporated by reference.

BACKGROUND OF THE INVENTION

The present invention relates generally to the field of medical devices. In particular, the present invention relates to devices for blood transfer, collection and sampling and methods for using the devices.

Frequent blood sampling is a required procedure for patients receiving fluids or medication through an arterial line and an indwelling catheter. In some patients, particularly neonates, drawing excess blood and the subsequent fluid flush can result in unacceptable changes in blood volume and pressure and poses a risk to the health of the infant. There are currently two methods for sampling blood from neonatal lines: the umbilical line blood draw by an umbilical arterial catheter (UAC) and the peripheral arterial line blood draw (PAL).

Both methods have considerable drawbacks. The foremost problem with both UAC and PAL is the volume of blood which must be withdrawn to obtain the sample. In order to obtain a clean sample of blood, sufficient blood must first be drawn into the sampling apparatus to clear the volume of dead space. In the current versions of both UAC and PAL systems this clearance volume is between 1.5 and 2.0 ml of blood. After the sample is taken it is necessary to return the clearance volume, then flush the system. The flush volume required can range from 0.5 ml to 2.0 ml. Therefore the total volume removed, returned and flushed for a neonate using these systems can be up to 5 ml or more. In low gram weight premature infants total blood volumes range from 60 to 80 ml. Rapid changes in blood volume from arterial blood sampling is proven to result in cerebral blood de-oxygenation and brain tissue de-oxygenation and can significantly affect neural development and is also known to be a major contributing factor to the development of cerebral palsy.

Another major drawback of current UAC systems is that 85% of samples drawn this way use an open stopcock in the apparatus and require multiple line accesses by opening and closing the system each time a syringe is replaced. This greatly increases the likelihood of contamination, and infection by bacterial, viral, and fungal sources. Further, using an open system also exposes the medical technician to the same infection risks.

Although PAL may be more convenient and practical, in many cases it is not possible to use with neonates. Current practice in PAL sampling also involves guesswork on the part of the technician drawing the blood since it is customarily measured by drops of blood, and is very inconsistent in the amount required to obtain a clearance of the line prior to sampling. Wasted blood from an open port is an exposure risk to the caregiver and the inclusion of sharp needles in the procedure for insertion into a T-connector results in needle sticks and exposure.

Existing closed-system blood sampling devices tend to be complex and require operation of multiple stopcocks, valves, and sampling sites present in the arterial line to accomplish the blood draw procedure. This complexity increases the risk of human error, of patient complications such as IVH (intraventricular hemmorage) and PVL (periventricular leukomalacia) and often requires the use of more flush volume than is desirable.

It is desirable to minimize these problems by using a blood sampling device that requires a low volume of blood and has a closed-system without the use of needles. The present invention requires very minimal clearance/waste (0.5 ml) and very minimal flushing (0.2-0.5 ml) after drawing blood from an indwelling catheter. Flushing is very minimal using the UAC and is not necessary after drawing blood from an indwelling PAL catheter.

RELEVANT ART REFERENCES

United States Patent Publication No. 2012/8152786 Shapland discloses a collection catheter and kit.

United States Patent Publication No. 2012/8096958 Sarstedt discloses a blood collection device for newborn babies and infants.

United States Patent Publication No. 1999/5916202 Haswell discloses a device and method for umbilical cord blood collection.

United States Patent Publication No. 1999/5893834 Duchamp discloses a self-filling blood collection device.

United States Patent Publication No. 1977/4024857 Blecher discloses a micro blood collection device.

These and all other referenced patents or publications are incorporated herein by reference in their entirety. Furthermore, where a definition or use of a term in a reference, which is an incorporated reference here, is inconsistent or contrary to the definition of that term, the term provided herein applies and the definition of that term in the reference does not apply.

BRIEF SUMMARY OF THE INVENTION

The disclosed embodiments provide a device for low-volume blood collection that reduces the risk of infection in patients and caregivers by maintaining the entire system in a closed state and by minimizing the number of line accesses required to collect blood.

One embodiment of the device includes a blunt, small bore transfer tube with twin micro bore tubing extensions attached. One tube extension is for holding and containing clearance blood, and one tube extension is for transfer of a blood sample to an attached collection device, i.e. syringe. The device is made for insertion of the blunt transfer tube through a split septum of a T-connector, and into the catheter hub to rest within 1-2 mm of the opening of the indwelling arterial catheter. The system requires only 0.5 ml for clearance and this reduction in blood volume is clinically important for patients that are volume restricted or that have low blood volumes.

After a blood draw from a pressure monitored umbilical artery catheter, it is routinely required that the line and catheter be flushed. The flush volume in existing systems can be up to 2.0 ml and is usually not less than 1.5 ml. The invention disclosed herein reduces flush volume to approximately 0.2 ml to 0.5 ml. No system on the market today can provide for such a low volume of clearance and such a low volume of flush to accomplish an arterial blood draw. There is also no interference with waveform obtained from the monitored line as there are no parts of the blood transfer device that are required to be in line with the hemodynamic monitoring setup and no blood is drawn up into the arterial line for clearance. Furthermore, although the device functions primarily for the withdrawal of small amounts of blood and standardizes the amount of blood wasted per draw to less than 0.5 ml, it does not necessarily limit the amount of blood that can be withdrawn from a patient.

The device is disposed as a closed system. It has no indwelling parts or stopcocks that reside in or on the arterial catheter line that could represents points of exposure to the atmosphere. The capillary-size blunt transfer tube is introduced into the line through the split septum T connector. The system is never open to the air and thereby greatly reduces the risk of infection. Further, since the collection tube for access to the system is blunt, this greatly reduces the risk of needle stick injury.

The device also reduces the number of line accesses required to do an arterial blood draw. Typically there are four line accesses required to do an arterial blood draw from a stopcock attached to an arterial indwelling catheter. First, attach a syringe for waste collection. Second, remove waste syringe and attach a syringe for sample collection. Third, remove sample syringe and re-attach waste for infusion back to patient and fourth, remove waste syringe and attach flush syringe and flush line. This represents a total of 4 accesses to an open port for an arterial blood draw. The disclosed invention reduces the number of line accesses to a single access through a closed port for any blood draw. This 75% reduction in line accesses (from 4 to 1) gives a clinically significant reduction in infection risk compared to any other system on the market today, open or closed.

Drawing blood with the disclosed invention also places no aspirating pressure on the artery in which the catheter indwells. The device is completely passive in its collection of blood, and creates no negative pressure on the artery when used properly with any self venting syringe. This reduces the risk for excessive aspirating pressure which can be a result of improper use of an aspirating syringe. Using non-aspirating syringes also eliminates air in the sample which can cause sampling errors. Use of self-venting syringes also eliminates air in the clearance blood, which could result in air being introduced into the patient when the clearance blood is returned to the patient. Reducing the volume needed for clearance also reduces the risk for creating excessive negative pressures in the vasculature of the patient from larger volume blood draws, and may reduce ischemic occurrences in the brain that have been demonstrated after an arterial blood draw from an umbilical line.

The manners in which the invention achieves its objects and other objects which are inherent in the invention will become more readily apparent when reference is made to the accompanying drawings wherein like numbers indicate corresponding parts throughout.

BRIEF DESCRIPTION OF THE DRAWINGS

FIG. 1 is a perspective view of a preferred embodiment of the invention separated from a commercially available catheter used for blood pressure monitoring.

DEFINITIONS

As used herein, "sampling" or "collection" includes removing a small amount of fluid for the purposes of testing, analyzing or storing.

A "port," as used herein, is a connection for communication of fluid. A port may be an inlet or an outlet. Fluid may be communicated and guided between two components by entering one port and exiting through another port.

A "stopcock" is a device having multiple ports and selectively allows fluidic communication at least between two ports.

A "syringe" refers to a device adapted to draw in, collect or eject out fluids.

A "solution" refers to a solution adapted to be supplied to a patient's blood stream. The solution may include infusion solutions including medication or fluids containing minerals to replenish a patient, for example. Solutions may also be adapted for flushing an arterial pressure monitoring line, for example.

A "reservoir" refers to a supply of fluid. The fluid may be stored for future use and may be accessible by another component.

As used herein, a "flush solution" is a fluidic solution adapted to flush, clean or sterilize certain components. The flush solution may include a saline solution, for example.

A "sampling site," as used herein, refers to a component which allows for the injection or withdrawal of a fluid from a line or tubing. A sampling site may be adapted to receive a blunt cannula or a needle to inject or withdraw fluid. As used herein, "sampling site" may also include a valve adapted to allow injection or withdrawal of fluids or a split septum.

DETAILED DESCRIPTION OF THE INVENTION

The micro-volume blood transfer device, a MVBTD 20, is depicted in FIG. 1. MVBTD 20 is disposed with a capillary-size transfer tube between 18-24 gauge, but which is preferably a 20 gauge micro bore transfer tube 21 between 30-40 mm in length with a blunt tip, 0.9 mm in outer diameter and 0.584 mm in inner diameter in a preferred embodiment. The micro bore transfer tube 21 is bonded to a Y-Connector 22, 24 mm in total length with 10 mm that serve as the male component to the hub holding the micro bore transfer tube 21. The Y-connector 22 is attached to micro bore extension tubes 23, which have a 1.9 mm outer diameter and a 0.9 mm inner diameter, and are 42 mm in length, in a preferred embodiment, but could range between 20-65 mm in alternative embodiments. The length of the micro bore extension tubes 23 along with the blunt transfer tube 21 is calibrated to allow exactly the volume required to clear three times the dead space required to obtain clean blood, approximately 0.5 ml. The micro bore extension tubes 23 are disposed with a mini pinch clamp for the clearance side 24 and a mini pinch clamp for the sample side 34 are distinctly colored and labeled to enable the user to selectively fill either side of the device. One side is designated for collection of the clearance blood while the other is designated for the collection of the blood sample. Both micro bore extension tubes 23 are further disposed with female lures 25, which are a total of 22 mm in length in a preferred embodiment, but the micro bore extension tubes 23 could range in length from 5-70 mm in length in alternative embodiments. Finally each female lure 25 is capped with a porous plug 26 containing a 0.22 um filter in a preferred embodiment, but the porosity of the plug 26 could range from 0.22-3.0 um.

The MVBTD 20 is designed to be inserted through a split-septum T-connector 27 into the base of an arterial catheter hub 28, where the micro bore transfer tube 21 comes to rest 1-2 mm from the catheter opening 29. This allows for blood to flow into the micro bore transfer tube 21 directly from the indwelling arterial catheter 29, and does not allow fluid from the fluid filled catheter hub 28 or T-connector 27 to flow into the micro bore transfer tube 21. This by-passing of the catheter hub 28 significantly reduces the clearance volume required. The amount of clearance blood is precisely measured to be less than 0.5 ml, which is an acceptable clearance volume for an arterial line blood draw.

Detailed Description of Use for Peripheral Arterial Catheter Blood Sampling

The device can be used for a Peripheral Arterial Line (PAL) catheter blood draw. With both micro bore extension tubes 23 clamped shut, the device is inserted into a T-connector 27 attached to the catheter hub 28 coming to rest 1-2 mm from the catheter opening 29. In this embodiment the micro bore extension tube 23 on the clearance line side has a self-venting plug 26 attached which allows patient blood pressure to push blood into the clearance line, without utilizing any aspirating pressure. In other embodiments a self venting syringe or an aspirating syringe is attached to the clearance side of the device and the clearance side clamp 24 is released allowing blood from the catheter 29 to enter the micro bore transfer tube 21 and travel up the clearance side until it reaches the attached clearance collector 25. The amount of clearance blood required to clear all the dead space in the device is approximately 0.2 ml. In the preferred embodiment where the plug 26 remains in place the mini pinch clamp for the clearance side 24 does not have to be reapplied prior to a self-venting syringe being attached to the blood sample side, the mini pinch clamp for the sample side 34 is released allowing clean blood to flow up the micro bore collection tube 21 and into the syringe, filling it to the desired pre-set volume of blood. The mini pinch clamp for the sample side 34 is then re-applied. Multiple syringes and sample amounts could be taken if desired, i.e. blood gas, glucose, lab tests, which may require multiple syringes. When conducting a UAC draw, the mini pinch clamp for the clearance side 24 is released and the clearance volume of 0.5 ml is slowly returned to the patient. This is not required for PAL draws. The device is removed from the T-connector 27 and deposited within an appropriate waste container. Flushing the device is not required for a PAL draw and is a low 0.3 ml up to 0.5 ml for the UAC draw. If the device is going to be flushed after use, a flushing syringe can be attached to the valve port 31 in the blood pressure monitoring line 30. The current method has no interference with waveform obtained from the monitored line as there are no parts of the micro volume blood transfer device that are required to be in line with the hemodynamic monitoring setup.

Detailed Description of Use for Umbilical Artery Catheter Blood Sampling

The device can also be utilized to draw clean blood from a UAC. With both micro bore extensions tubes 23 clamped shut, the device is inserted into a T-connector 27 attached to the catheter hub 28 coming to rest 1-2 mm from the catheter opening 29. A self venting syringe is attached to the clearance side of the device, and the mini pinch clamp for the clearance side 24 is released allowing blood from the catheter to enter the micro bore transfer tube 21 and travel up the clearance side until it reaches the attached self venting syringe, pre-set to the desired clearance volume, approximately 0.5 ml of blood. This clearance volume clears all the umbilical catheter dead space and represents at least three times the catheter lumen fluid volume. The mini pinch clamp for the clearance side 24 is then reapplied, a second self venting syringe is attached to the blood sample side and the mini pinch clamp for the sample side 34 is released. When the mini pinch clamp for the sample side 34 is opened clean blood flows up the micro bore transfer tube 21 and into the syringe, filling to the desired pre-set volume of blood. The mini pinch clamp for the sample side 34 is then re-applied. After the sample is collected, mini pinch clamp for the clearance side 24 is released and the held clearance volume of 0.5 ml is slowly returned to the patient. The mini pinch clamp for the clearance side 24 is re-applied. The sample syringe with sample blood is then removed for testing. The device MVBTD 20 is removed from the T-connector 27 and deposited within an appropriate waste container. A 10 ml flush syringe may be attached to the valve port 31 at the end of the T-extension set. Only 0.5 ml is needed to flush the catheter after use so the 10 ml flush syringe only needs replacement after 15-20 blood draws, or once per day if a 10 ml flush syringe were used. This reduces multiple line accesses for flushing because there is no need to replace the flush syringe every time there is a blood draw, which in turn reduces the possibility of infection and contamination to the patient and caregiver. The current method has no interference with waveform obtained from the monitored line as there are no parts of the micro volume blood transfer device that are required to be in line with the hemodynamic monitoring setup.

It will be understood that various modifications can be made to the various embodiments of the present invention herein disclosed without departing from the spirit and scope thereof. For example, various devices are contemplated as well as various types of construction materials. Also, various modifications may be made in the configuration of the parts and their interaction. Therefore, the above description should not be construed as limiting the invention, but merely as an exemplification of preferred embodiments thereof. Those of skill in the art will envision other modifications within the scope and spirit of the present invention as defined by the claims appended hereto.

I claim:

1. A micro-volume blood transfer device, comprising: a micro bore transfer tube with a transfer tube distal opening and a transfer tube proximal opening wherein the transfer tube proximal opening is connected to a Y-connector, the Y-connector is further connected to a clearance line and a sample line wherein the clearance line has a mini pinch clamp and the sample line has a second mini pinch clamp and wherein the transfer tube distal opening is inserted through a catheter hub where blood from a patient is in fluid communication with a catheter opening and the transfer tube comes to rest within one-two millimeters of the catheter opening; and wherein the clearance line collects less than 0.5 milliliters of blood.

2. The blood transfer device of claim 1 wherein the sample line is capable of sampling a clean blood sample wherein the clearance line collects 0.5 milliliters of blood or less.

3. The blood transfer device of claim 1 further comprising; a female luer at a terminal end of the clearance line and a female luer at a terminal end of the sample line.

4. The blood transfer device of claim 1 further comprising; a female luer with a porous plug inserted in the terminal end of the clearance line and a female luer with a porous inserted in the terminal end of the sample line.

5. The blood transfer device of claim 1 wherein the micro bore transfer tube is between 18-20 gauge diameter.

6. The blood transfer device of claim 1 wherein the micro bore transfer tube is between 30-40 mm in length.

7. The blood transfer device of claim 1 wherein the clearance line and the sample line are comprised of a micro bore extension line between 5-70 mm in length.

8. The blood transfer device of claim 2 wherein, the sample line has a self venting syringe attached to the female luer, or any desired type of syringe for collection of fluid/blood.

9. The blood transfer device of claim 2 wherein, the sample line has a self venting syringe attached to the female luer and the clearance line has a self venting syringe attached to the female luer or any type of syringe for collection of fluid/blood.

* * * * *